US012702787B2

(12) United States Patent
Porges et al.

(10) Patent No.: US 12,702,787 B2
(45) Date of Patent: Aug. 11, 2026

(54) AUGMENTED REALITY COORDINATED WITH NERVE STIMULATION TO ENHANCE PERFORMANCE

(71) Applicant: UNIVERSITY OF FLORIDA RESEARCH FOUNDATION, INCORPORATED, Gainesville, FL (US)

(72) Inventors: Eric S. Porges, Gainesville, FL (US); John B. Williamson, Gainesville, FL (US); Damon Lamb, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 1064 days.

(21) Appl. No.: 17/792,533

(22) PCT Filed: Jan. 13, 2021

(86) PCT No.: PCT/US2021/013185

§ 371 (c)(1),
(2) Date: Jul. 13, 2022

(87) PCT Pub. No.: WO2021/146243

PCT Pub. Date: Jul. 22, 2021

(65) Prior Publication Data

US 2023/0001130 A1 Jan. 5, 2023

Related U.S. Application Data

(60) Provisional application No. 62/960,458, filed on Jan. 13, 2020.

(51) Int. Cl.

*A61M 21/02* (2006.01)
*A61B 5/00* (2006.01)
(Continued)

(52) U.S. Cl.

CPC ......... *A61M 21/02* (2013.01); *A61N 1/36078* (2013.01); *A61M 2021/005* (2013.01);
(Continued)

(58) Field of Classification Search

CPC ............ A61M 21/02; A61M 2021/005; A61M 2021/0072; A61M 2230/62;
(Continued)

(56) References Cited

U.S. PATENT DOCUMENTS 6,425,764 B1 7/2002 Lamson
9,001,036 B2 4/2015 Sugaya et al.
(Continued)

FOREIGN PATENT DOCUMENTS

WO 2014039569 A2 3/2014
WO 20151262191 A1 8/2015
(Continued)

OTHER PUBLICATIONS

PCT Search Report & Written; PCT/US2021/013185; mailed May 6, 2021, 13 pages.

*Primary Examiner* — Carrie R Dorna
*Assistant Examiner* — Joshua Daryl D Lannu
(74) *Attorney, Agent, or Firm* — Timothy H. Van Dyke; Wolter Van Dyke Davis, PLLC

(57) ABSTRACT

Disclosed herein are systems and methods for increasing performance, improving sleep and improving relaxation that involve specifically coordinating nerve stimulation of a cranial nerve (e.g. vagus nerve) in conjunction with augmented reality (AR). According to certain embodiments disclosed are systems that include an AR component that presents information or a stimulus and provides cranial nerve fiber stimulation (CNFS) at strategic times to reduce anxiety/arousal/related during user activity or scenarios and reinforce learning.

19 Claims, 7 Drawing Sheets

(51) Int. Cl.

| | |
|---|---|
| ***A61B 5/11*** | (2006.01) |
| ***A61B 5/369*** | (2021.01) |
| ***A61M 21/00*** | (2006.01) |
| ***A61N 1/36*** | (2006.01) |

(52) U.S. Cl.
CPC . *A61M 2021/0072* (2013.01); *A61M 2230/62* (2013.01); *A61M 2230/63* (2013.01)

(58) Field of Classification Search
CPC ........ A61M 2230/63; A61M 2205/332; A61M 2205/3375; A61M 2230/04; A61M 2230/06; A61M 2230/10; A61M 2230/30; A61M 2230/42; A61M 2230/50; A61M 2230/60; A61N 1/36078; A61N 1/36025; A61N 1/36096; A61N 1/36053; A61N 1/36057; A61N 1/36092; A61B 5/1107; A61B 5/1118; A61B 5/369; A61B 5/4809
See application file for complete search history.

(56) References Cited

U.S. PATENT DOCUMENTS

| | | | | |
|---|---|---|---|---|
| 10,147,218 | B2 | 12/2018 | Alkouh | |
| 10,232,178 | B2 | 3/2019 | Simon et al. | |
| 2012/0110516 | A1 | 5/2012 | Tumanov | |
| 2014/0228905 | A1* | 8/2014 | Bolea | A61F 5/56 607/42 |
| 2017/0193169 | A1 | 7/2017 | Davis et al. | |
| 2017/0361097 | A1* | 12/2017 | Williamson | A61N 1/36025 |
| 2018/0292888 | A1 | 10/2018 | Slepian et al. | |
| 2019/0001117 | A1* | 1/2019 | Ben-David | A61N 1/0534 |
| 2019/0117933 | A1 | 4/2019 | Couser | |
| 2019/0201707 | A1 | 7/2019 | Stubbeman | |

FOREIGN PATENT DOCUMENTS

| | | | |
|---|---|---|---|
| WO | 2017173331 | A1 | 10/2017 |
| WO | 2019060298 | A1 | 3/2019 |

* cited by examiner

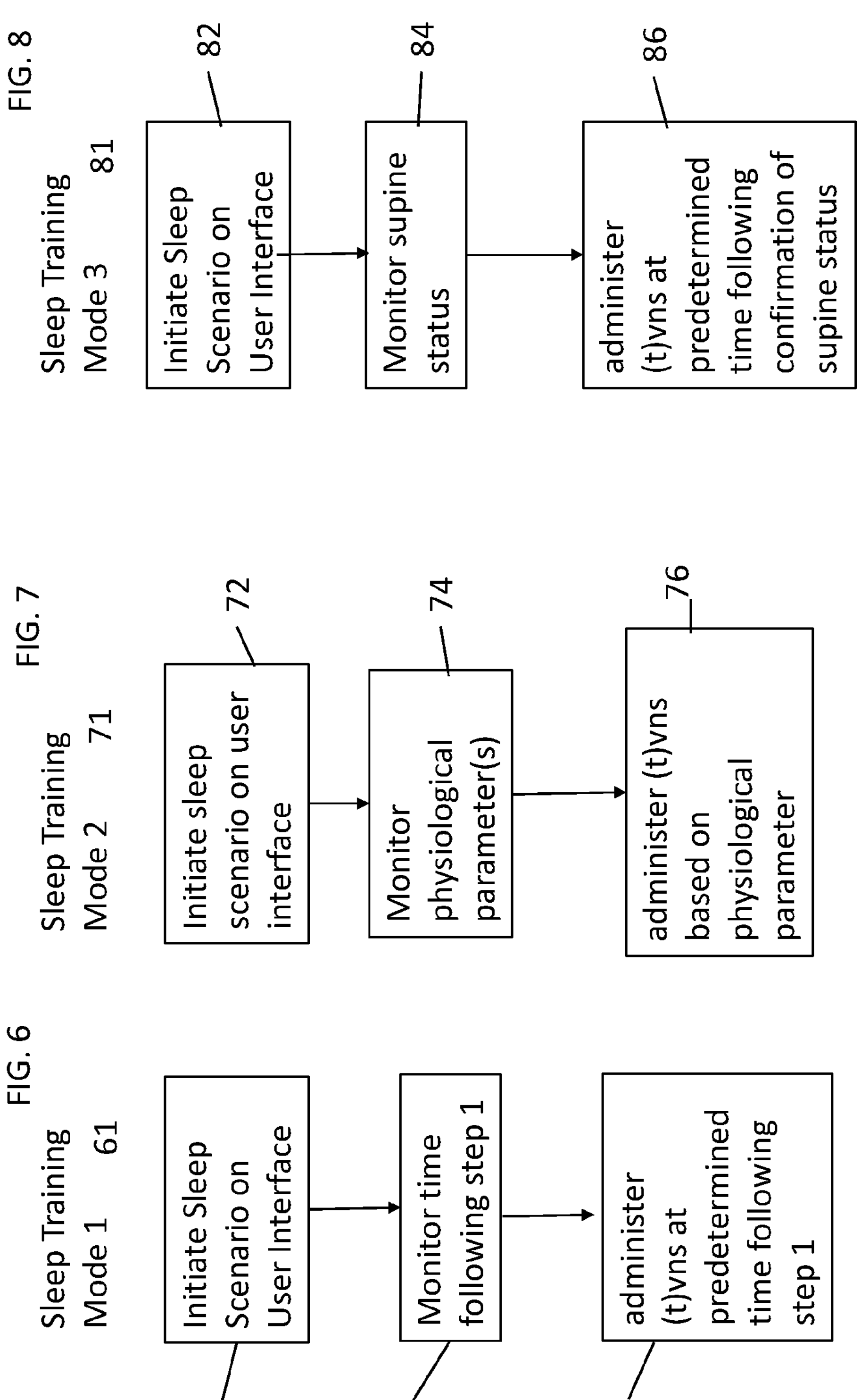
FIG. 6
Sleep Training Mode 1
61
Initiate Sleep Scenario on User Interface
62
Monitor time following step 1
64
administer (t)vns at predetermined time following step 1
66
FIG. 7
Sleep Training Mode 2
71
Initiate sleep scenario on user interface
72
Monitor physiological parameter(s)
74
administer (t)vns based on physiological parameter
76
FIG. 8
Sleep Training Mode 3
81
Initiate Sleep Scenario on User Interface
82
Monitor supine status
84
administer (t)vns at predetermined time following confirmation of supine status
86

For a 20 year old male, normative RSA is 6.74 ms stdev +/- 1.24
Going through a 15minute, recorded audio, guided, body scan meditation.

FIG. 9

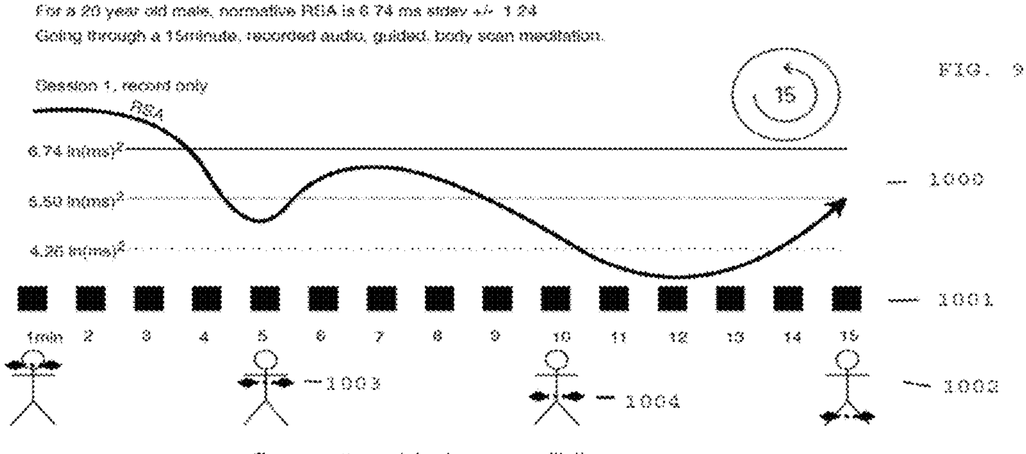

Progress through body scan meditation

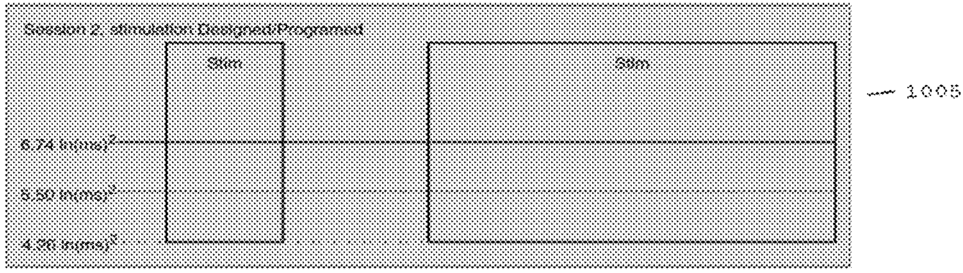

Session 2, stimulation deployed and RSA recorded, while same body scan mediation is engaged in

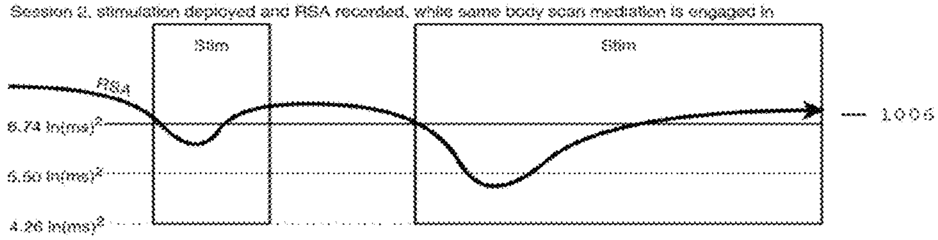

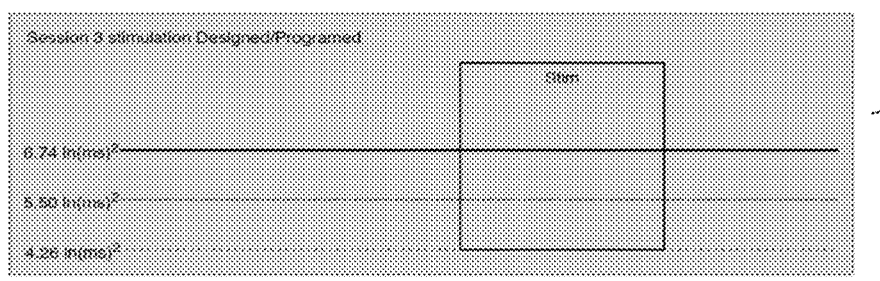

Session 3, , stimulation deployed and RSA recorded, while same body scan mediation is engaged in

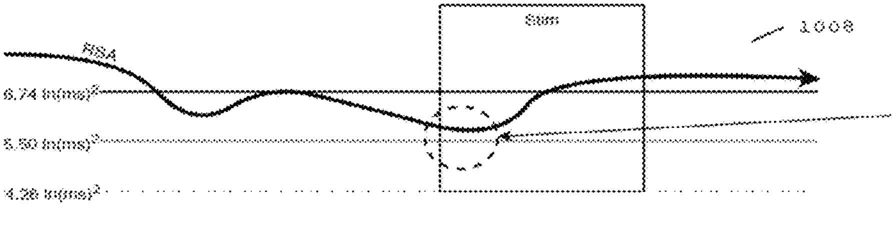

Repeat...

Note that RSA is never less than 1 stdev below average, hence no stimulation will be delivered in next Session, though recording may continue and stimulation would be delivered in future sessions if it fell below threshold again At times/epochs where there is historical evidence (or population based evidence) of increased incidence of RSA decrease, the system may be biased to increase likely hood of stimulation. one implimentation may be that a reduced threshold is used during that time period (e.g. 0.5 stdev). Another approach may be that stimulation remains in place for 2 or more sessions, even if rsa ceased to be below threshold.

AUGMENTED REALITY COORDINATED WITH NERVE STIMULATION TO ENHANCE PERFORMANCE

BACKGROUND

Vagus nerve stimulation and its non-invasive (tVNS) counterparts, e.g., transcutaneous (tVNS) or transcutaneous auricular vagus nerve stimulation (taVNS), are known and have been used to treat neurological disorders such as epilepsy or psychological/psychiatric disorders such as depression and post-traumatic stress disorder (PTSD). Systems have been devised to control the provision of (t)VNS based on certain physiological feedback. US Pat. Pub No. US20170361097 describes, among other things, systems that optimize the level of vagus nerve stimulation based on changes in respiratory sinus arrythmia or other markers of physiological impact of vagus nerve stimulation. While benefits of (t)VNS are recognized, the potential applications and implementations of (t)VNS have not been fully explored.

BRIEF DESCRIPTION OF THE DRAWINGS

FIG. 6 provides a flow diagram of method involving (t)VNS implemented to induce or improve sleep.

FIG. 7 provides a flow diagram of a method involving (t)VNS implemented to induce or improve sleep.

FIG. 8 provides a flow diagram of a method involving (t)VNS implemented to induce or improve sleep.

FIG. 9 provides a series of diagrams showing implementation of cranial nerve stimulation to modulate RSA in a body-scan mediation.

DETAILED DESCRIPTION

Figure 1:
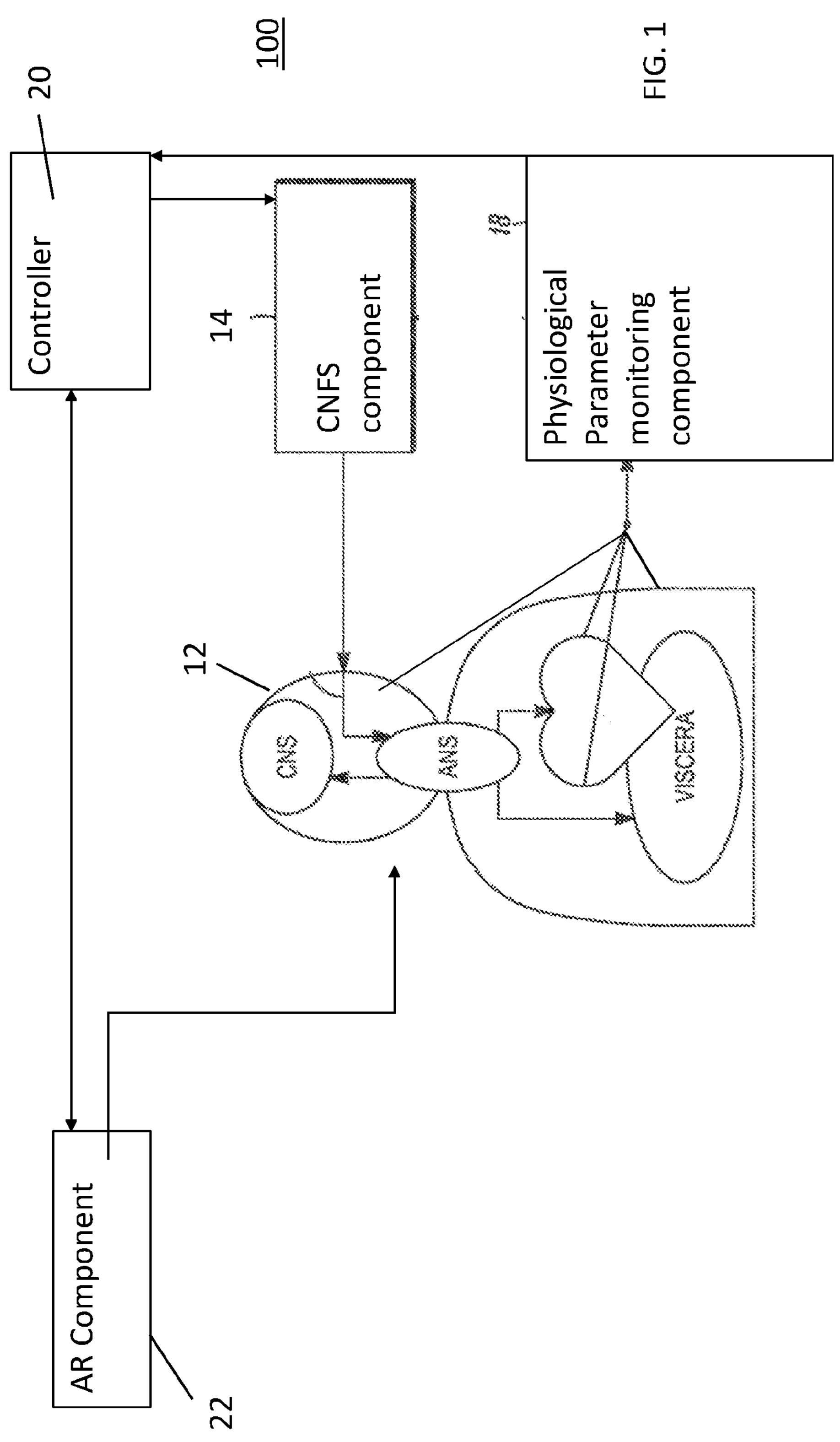
FIG. 1 provides a diagram of a system embodiment for providing CNFS in coordination with AR and physiological parameters.

Disclosed herein are systems and methods for increasing performance, improving sleep and improving relaxation that involve specifically coordinating nerve stimulation of a cranial nerve (e.g. vagus nerve) in conjunction with augmented reality (AR). According to certain embodiments disclosed are systems that include an AR component that presents information or a stimulus and provides cranial nerve fiber stimulation (CNFS) at strategic times to reduce or otherwise modulate anxiety/arousal of a subject during user activity or scenarios and/or to reinforce learning. According to certain embodiments, scenarios are repeated or rehearsed in substantially the same manner over multiple sessions and can be performed in conjunction with measurement of physiological behavior, e.g. reduced heart rate variability (HRV, similar to hf-HRV, RSA, SDNN, RSDNN, etc.), which is reflective of anxiety or cognitive effort. The physiological response during that session can be used to determine when stimulation/modulation techniques such as vagus nerve stimulation (invasive or non-invasive) or similar methods such as trigeminal stimulation should be deployed to provide for 1) modulation of that anxiety/arousal response or 2) to facilitate neuroplasticity/learning of the less aroused state while the stimulation is applied. During subsequent sessions following an initial session, stimulation is delivered (as indicated by prior sessions physiological behavior (e.g. reduced HRV)) and is recorded and used to inform future sessions. In one example, administering central nerve fiber stimulation prior to recorded arousal time pertains to initiating central nerve fiber stimulation at a time within 1-30 mins, within 1-15 mins, or within 1-5 mins before the recorded arousal time.

This method has advantages over closed loop approaches in the ability to deploy stimulation before arousal/anxiety manifests, i.e. in anticipation rather than in response to it.

As will be explained further herein, CNFS can be deployed in Bodyscan meditation (BM)/Progressive relaxation (PR), Guided relaxation and related methods, and also in performance enhancement applications such as sports performance (e.g. rehearsal of golf putting), defense related applications (e.g. rehearsal of shooting a rifle), as well as in the treatment of phobias (e.g. during rehearsed visualization or Virtual reality exposure therapy for fear of flying, heights, public speaking, substance abuse, etc).

Definitions

The term "cranial nerve fiber stimulation" or "CNFS" refers to stimulation of one or more cranial nerves. In specific embodiments, the cranial nerve stimulated pertains to the vagus nerve, trigeminal nerve and/or hypoglossal nerve. CNFS may be applied to afferent fibers (i.e., fibers sending signals to the central nervous system (CNS)) and/or efferent fibers (i.e. fibers sending signals away from the CNS, such as to a target organ. Both peripheral and central effects can be achieved. The physiological indicators of the periphery reflect the behavior of brain systems that regulate them. Directly modifying function of peripheral systems via efferent stimulation will contribute to communication of a relaxed state to the central nervous system. Stimulation of the afferent path will influence the behavior of the brain systems that regulate the peripheral signals. Further, the CNFS can involve both sensory subthreshold and suprathreshold stimulation.

The term "autonomic nervous system" or "ANS" refers to a neural control system that acts largely unconsciously and regulates bodily functions such as the heart rate, digestion, respiratory rate, pupillary response, urination, and sexual arousal. The autonomic nervous system is divided into three parts: the sympathetic nervous system, the parasympathetic nervous system and the enteric nervous system.

The term "augmented reality" or "AR" as used herein refers to computer controlled sensory information presented to a user. AR may comprise visual, auditory, vestibular, haptic, gustatory, olfactory, pain, temperature, kinesthetic or other sensory stimulation, secondary activities, thought processes, visual thinking, verbal thinking, emotions, medications, chemicals, physiological manipulations, neurofeedback, psychotherapy, videoconferencing, video recordings, social interaction, virtual reality ("VR"), or guided imagery. Typically, AR will involve simulation of a real-life event or activity and will involve provision of information via one or multiple sensory modalities, including visual, auditory, haptic, somatosensory and/or olfactory.

The term "AR component" refers to any device that is capable of providing AR to a user. Examples of AR components may include a visual display, speaker, haptic devices including but not limited to gyroscope or vibrator component, temperature generator, pressure generator, and the like, and combinations thereof. In a specific embodiment, the AR component may comprise a biofeedback component.

The term "biofeedback" as used herein refers to a signal, such as electrical, audible, visual, or sensory, that is delivered to a user in response to a previous action taken by the user. Biofeedback is typically utilized in an effort to train the user to exert some level of control over an involuntary body function such as heart rate, brain waves, anxiety and muscle tension, or other physiological functions.

The term "biofeedback component" is a component that provides biofeedback to a user.

The term "physiological parameter" refers to any measurable or detectable physiological indicator of a subject. Examples of physiological parameters include, but are not limited to heart rate, heart rate variability (HRV), temperature, neural activity (e.g. EEG, ECG), respiratory sinus arrhythmia (RSA), galvanic skin response (GSR) respiratory hippus variability (RHV) and gastric movement, e.g.,via use of electrogastrography (EGG) or other techniques to determine gut motility. Physiological parameters may also include respiration, respiratory variability, blood pressure, blood pressure variability, pulse wave size, slope, etc, pulse variability, body tonicity (alteration in body movement), tremor/repetitive motor activity, pilo-erection, reproductive organ behavior, EGG: Electrogastrogram (and other measures of gastric movement), fMRI, EEG and other measures of direct neural behavior. Physiological parameters can also include skin temperature change or skin conductance.

The term "physiological parameter monitoring component" as used herein refers to any sensor and/or device that is capable of detecting and/or monitoring a physiological parameter. Examples of physiological parameter monitoring components include, but are not limited to, a pulse oximeter, photoplethysmography sensor, ECG/EKG sensor, EEG sensor, EMG sensor, respiratory sensor, acoustic sensor (e.g. microphone), camera, EGG sensor, accelerometer, thermometer, electrodes, and the like.

The term "user activity output" refers to any activity of the user that is not a physiological parameter. Examples of user output include user movement, user sounds, spatiotemporal positioning, and/or timing and accuracy of the foregoing. Such user activity output may include activity in response to a prompt, question, trigger, etc. whether from system (e.g. AR component) or third party, or derived indices (e.g. reaction time variability or accuracy) related to generation of a response.

The term "user activity output monitoring component" as used herein refers to any device and/or sensor that is capable of detecting user output. Examples of a user output monitoring component include, but are not limited to a camera, a microphone, spatiotemporal sensors, accelerometers, gyroscope, thermometer, or ultrasound.

The term "vagus stimulation" pertains to a specific embodiment of CNFS and refers to stimulation of afferent or efferent or both fiber types of the vagus nerve. Vagus stimulation may be conducted transcutaneously ((t)VNS) or internally, i.e. implanted.

The term "user" refers to any human or non-human mammal to which CNFS is applied according to the teachings herein.

The term "controller" as used herein refers to any computing device that is capable of being programmed to conduct operative functions, as well as receiving, processing and sending electrical signals, either via wires or wirelessly. A controller may further include a timer component.

The term "aroused state" as used herein refers to a state where change in the physiological parameter has occurred. In some domains (e.g. RSA) normative data may exist and be used, however this may also be established in the individual based on baseline (pre-task or at another time/location) measurement of the physiological parameter. Accordingly, an aroused state may be state specific, e.g., supine, seated or standing specific; that is the measures or determination of an "aroused state" may vary based on body position, even when "resting", which can be detected using various sensors such as accelerometer(s), gyroscopes, etc. These changes may be characterized as exhibiting a predefined range of a detected physiological parameter value, or by the magnitude or rate of change. An aroused state may also be determined by observing decreases in RSA/hf-hrv/etc., or increases in sympathetic nervous system activity (e.g. pulse amplitude, skin conductance, heart rate, measures derived from impedance cardiography—such as pre-ejection period, blood pressure), or even subjective or behavioral indication of aroused state. In one example, administering central nerve fiber stimulation prior to recorded time of an aroused state pertains to initiating central nerve fiber stimulation at a time within 1-30 mins, within 1-15 mins, or within 1-5 mins before the recorded arousal time.

Description of Illustrated Embodiments

For the purposes of promoting an understanding of the principles and operation of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to those skilled in the art to which the invention pertains.

It is to be noted that the terms "first," "second," and the like as used herein do not denote any order, quantity, or importance, but rather are used to distinguish one element from another. The terms "a" and "an" do not denote a limitation of quantity, but rather denote the presence of at least one of the referenced item. The modifier "about" used in connection with a quantity is inclusive of the stated value and has the meaning dictated by the context (e.g., includes the degree of error associated with measurement of the particular quantity). It is to be noted that all ranges disclosed within this specification are inclusive and are independently combinable.

The terminology used herein is for the purpose of describing particular embodiments only and is not intended to be limiting. As used herein, the singular forms "a," "an," and "the" are intended to include the plural forms as well, unless the context clearly indicates otherwise these terms do not denote a limitation of quantity, but rather denote the presence of at least one of the referenced item. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order, quantity or importance, but rather the terms first, second, etc., are used to distinguish one element from another.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation, or other variance found in their respective measurements. Moreover, all ranges disclosed herein are to be understood to encompass any and all sub-ranges subsumed therein. As a non-limiting example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 7.

FIGS. 1, 2, 3, and 4 illustrate system embodiments 100, 200, 300 and 400, respectively.

FIG. 1 illustrates an exemplary embodiment of a system 100 that includes an CNFS component 14, a physiological parameter monitoring component 18, a controller 20 communicably connected to the CNFS component 14 and physiological parameter monitoring component 18, and a augmented reality (AR) component 22 that may also be communicably connected to the controller 20. The system 100 also optionally includes a User activity output monitoring component 24 that is capable of monitoring user output from the user 12.

The physiological parameter monitoring component 18 is configured to sense or measure physiological parameter signals from the user 12. The controller 20 is preferably configured to receive input from AR component 18 and transmit an output to the CNFS component. The controller 20 includes a central processing unit, circuitry for receiving/sending electrical signals and/or user input and at least one memory device, wherein the controller coordinates the operation among the different parts of the system 100, and optionally adjust stimulation parameters in real-time and deliver the output to the subject to enhance reduction of anxiety, for example. The controller 20 may also be equipped with a user interface and timer component. As another example, the controller 20 may include one or more software algorithms that control operation of the various components 18, 14, and 22 for a given scenario. For example, the controller 20 may initiate provision of an AR from the AR component 22 and, based on a predetermined time in the AR scenario, a certain AR event in the AR scenario, and/or the physiological parameter monitoring component 18 detecting one or more triggering parameters, the controller 20 directs the CNFS component 14 to administer CNFS to the user 12. Examples related to implement the system 10 to increase performance, relaxation, treat phobias, or induce deeper relaxation are provided in the Examples section below.

The controller 20 may also be programmed to modify the intensity or duration of the CNFS to a level optimized to achieve the intended effect, while also reducing discomfort. Applicants cite to US Pat. Pub No. US20170361097 for teachings of modulating (t)VNS based on detected changes in physiological parameters such as respiratory sinus arrythmia (RS), which is incorporated herein in its entirety. The controller may also be programmed with safety measures to shut down CNFS based on a physiological parameter exceeding a predetermined threshold.

Figure 2:
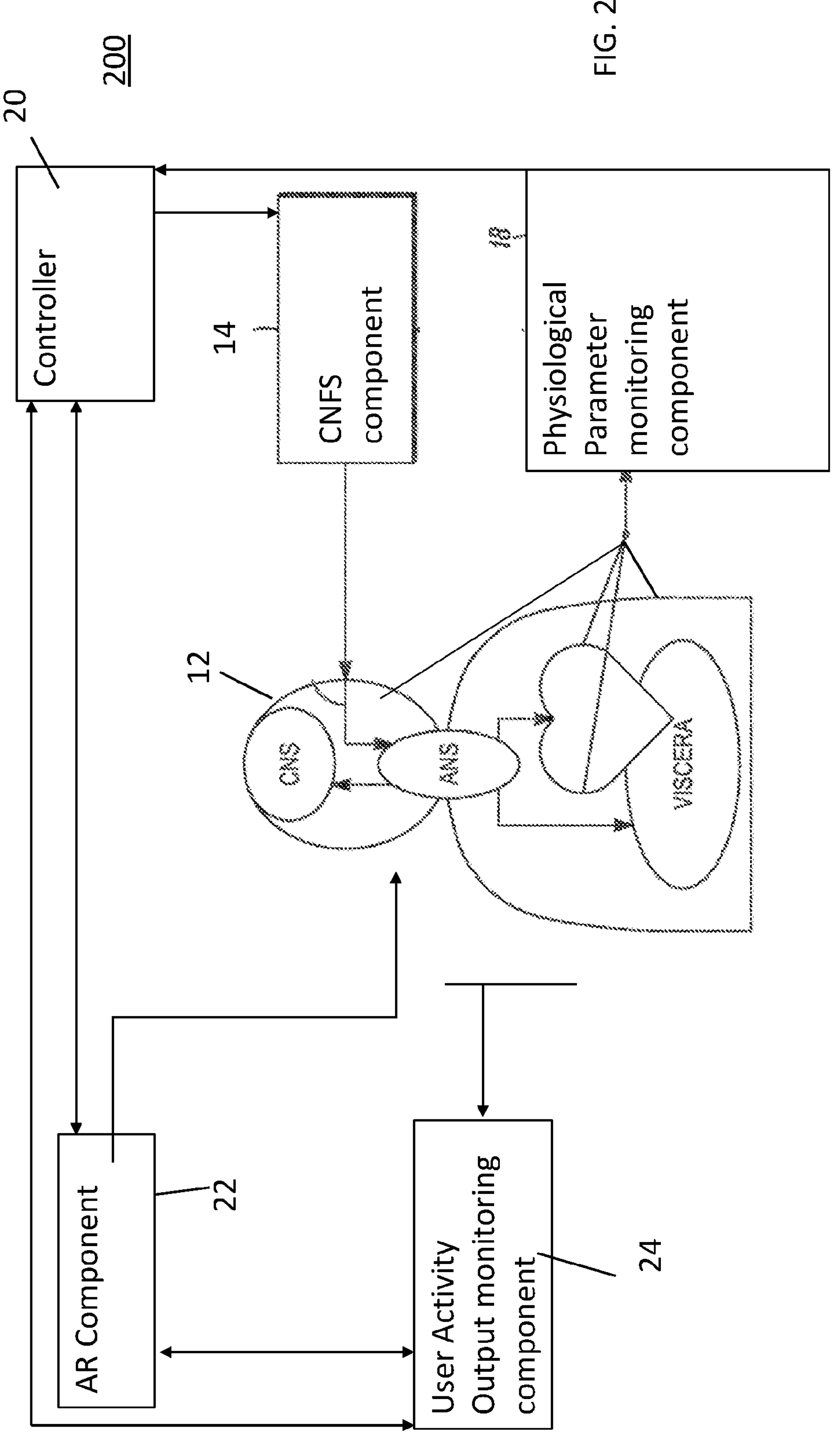
FIG. 2 provides a diagram of a system embodiment for providing CNFS in coordination with AR and User activity output.

The AR component 22 may provide sensory stimulation to the user 12 before, during, or after CNFS or at targeted times during an AR scenario. Examples of sensory stimuli provided by the AR component 22 may include music, white noise, individually selected emotionally uplifting music to treat depression or enhance cognition; trauma-related virtual-reality stimulation, haptic stimulation of specific dermatomes for treatment of chronic pain syndromes; physical exercises; guided virtual-reality experiences or recorded video stimulation of athletic performances to enhance motor skills; guided mental exercise instructions to enhance cognitive skills; video-conferenced psychotherapeutic treatment (including cognitive behavioral therapy); guided imagery; guided meditation to enhance psychological skills; or guided simulations of social situations to enhance social skills or autism spectrum disorders. Known AR components 22 that may be used in one or more aspects of the exemplary embodiments include headphones, speaker(s), monitor(s) displaying video recordings, or virtual-reality devices or systems As shown in FIG. 2, the system 200 provides a system that includes an CNFS component 14, controller 20, physiological parameter monitoring component 18, and AR component 22 as described above for FIG. 1, but also includes a user activity output monitoring component 24. Component 24 may comprise any of a number devices that monitor user activity not pertaining to physiological parameters such as movement, spatiotemporal positioning, sounds, facial expressions and the like. Detected user activity is sent to the controller 20, which can in turn, control, time or synchronize the provision of AR and/or CNFS based on the detected user activity. The controller 20 may be equipped with programming for detecting user activity, and optionally, the system (e.g. user activity output component) may include devices worn by the user to assist in detection of such user activity (e.g. accelerometers, tilt sensors, color markers such as fluorescent stripes or circles, and the like). Examples of such devices are described in US Pat. Pub 20120110516, KR pat pub 2015001737, U.S. Pat. No. 9,001,036, and U.S. patent Ser. No. 10/147,218, which are incorporated herein in their entirety. In an alternative embodiment of system 400, the AR component 22 is omitted.

The principles described herein of using a psychological state or an elicitor of a psychological state (such as an external stressor) can be implemented for improving eating, gastrointestinal/digestion behavior/function. For example, a subject could report an eating event (e.g. predetermined scheduled time for eating or when eating has occurred) to the controller 20, and/or an eating related activity (e.g. utensil moved, eating sounds, mouth movement, swallowing, etc.) can be sensed by the user activity output monitoring component 24, and/or GI signals (movement of gastrointestinal tract, gastrointestinal sounds, etc) can be sensed by the physiological parameter monitoring component 18. Anticipatory stimulation from the CNFS component 14 (based on a schedule/time) or stimulation from the CNFS component 14 after an eating event or GI signal can be applied to induce eating or gastrointestinal activity. Typically, for improving eating or GI function, the CNFS component applies the appropriate stimulation to the relevant vagus fibers. Alternatively, the physiological parameter monitoring component is configured to detect blood state or blood state changes relating to eating or GI function, and stimulation for CNFS component can be automatically applied in response to blood state or blood state changes.

Figure 3:
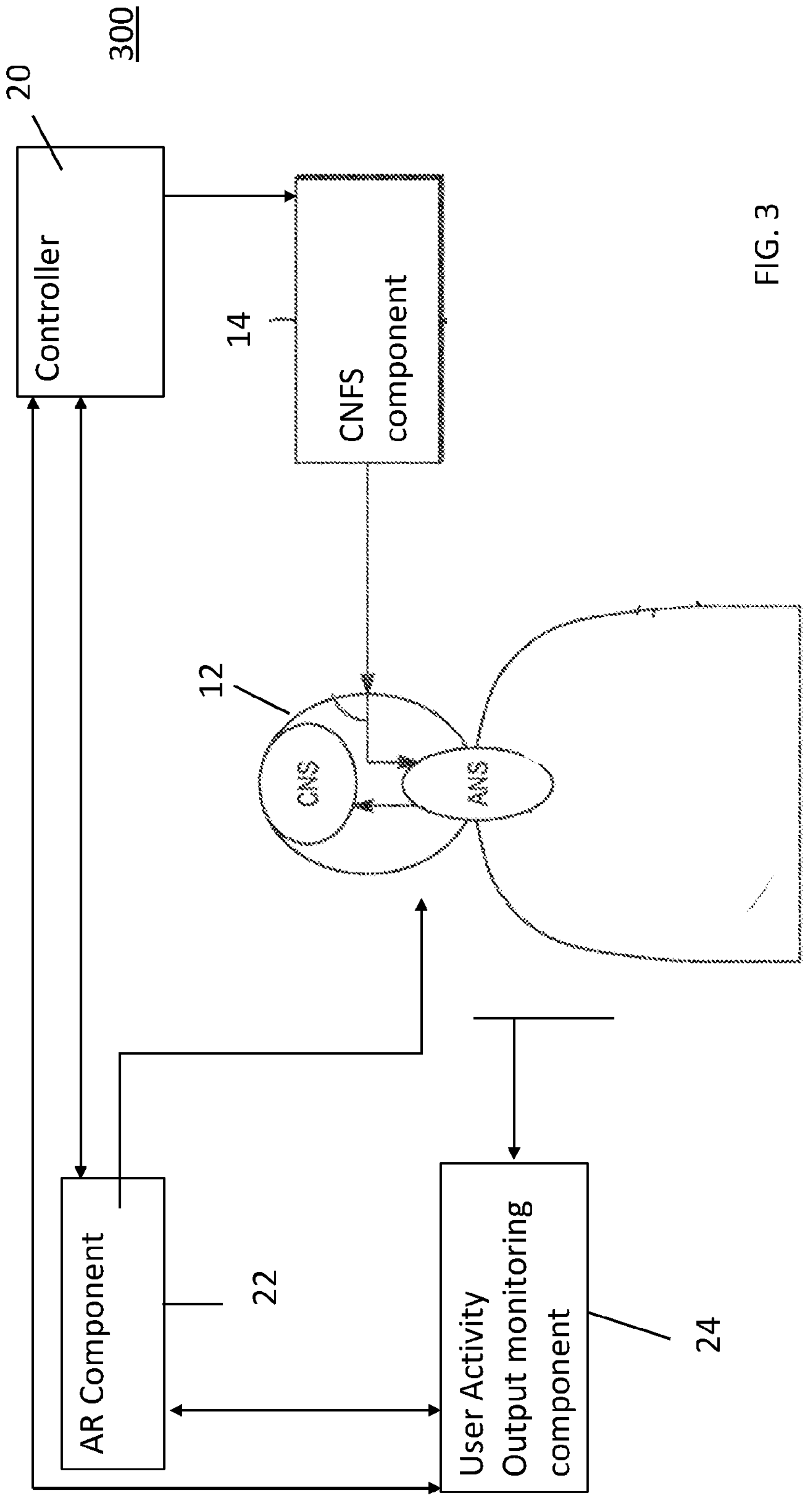
FIG. 3 provides a diagram of a system embodiment for providing CNFS in coordination with AR and/or user activity output independent of physiological parameter monitoring.

As shown in FIG. 3, the system 300 includes an CNFS component 14, controller 20, an AR component 22 and, optionally, an user activity output monitoring component 24 as described above for FIG. 2, but where the system 300 lacks a physiological parameter monitoring device 18. In this embodiment, the controller 20 can be programmed to provide CNFS at a certain time or times during an AR scenario provided by the AR component 22. There may be situations or conditions where it is preestablished that at the certain time within an AR scenario anxiety is induced, and CNFS can be strategically administered to reduce user anxiety, induce relaxation, increase performance etc. without the need for physiological monitoring. The system 300 may optionally include the user activity output monitoring component 24 where CNFS is strategically administered before, after or during a certain movement or series of movements, positioning, expression or the like, without the need for physiological monitoring.

Figure 4:
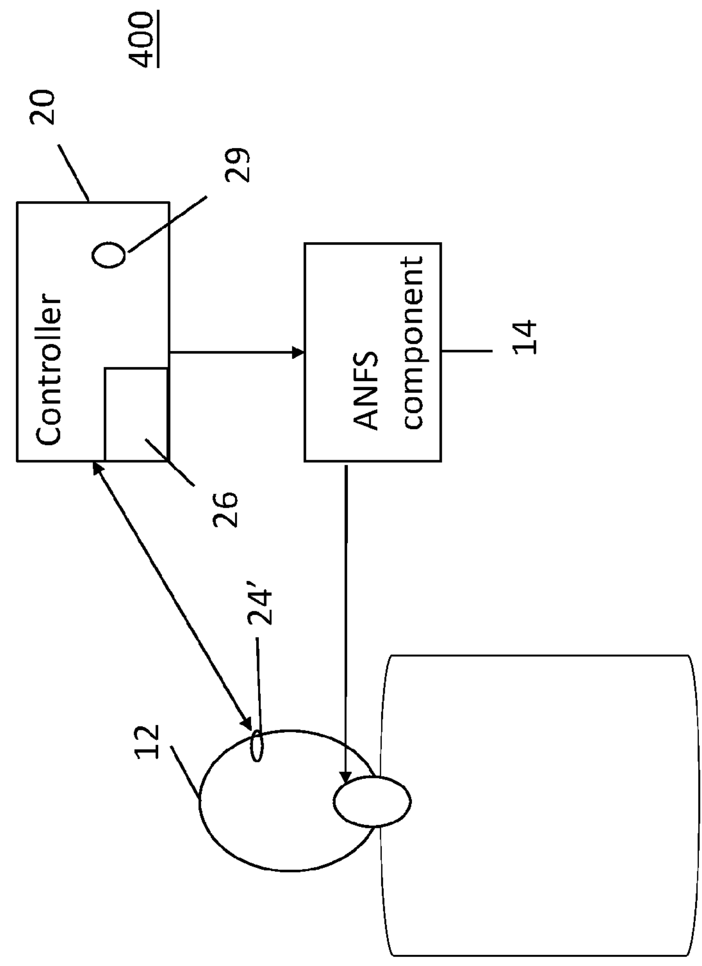
FIG. 4 provides a diagram of a system embodiment for providing CNFS in coordination with time lapse or positioning of user.

FIG. 4 illustrates a system embodiment 400 that includes a controller 20, an CNFS component 14 and an optional user activity output monitoring component 24'. In this embodiment 400, CNFS is administered based on signals from the user activity output monitoring component 24'. The user activity output monitoring component 24' may take the form of any example described above for 24, or as is shown in FIG. 4, is a device worn by the user. System embodiment 400 strategically administers CNFS as a function of a predetermined user activity output, that does not necessarily involve AR. For example, system 400 can be especially adapted for inducing sleep or increasing quality of sleep. The user activity output monitoring component 24' can take the form of a tilt sensor or accelerometer or other sensor whether or not physically attached to the user (such as a sensor on a mat or bed or via non-contact sensors) that can detect the position of the user, namely whether the user 12 is in a supine position. The user activity output monitoring component 24' may pertain to a sensor to detect sleep initiation, time of day, light sensor, polysomnography, electroencephalograph (EEG), or subject interaction with interface to initiate sleep mode. The user 12 via a user interface 26 associated with the controller 20 can initiate the session such that the controller 20 begins sensing the position of the user 12. Upon sensing that the user 12 is in a supine position, the controller 20 will initiate CNFS by the CNFS component 14 at a predetermined time (e.g. 10-25 min) following supine positioning. The controller 20 can be programmed to administer CNFS for predetermined time frame, or series of time frames. The intensity and/or duration of CNFS can be adjusted to meet the circumstances and implementation. The user interface 26 may include touch inputs, dials, lights, sound, and/or display to facilitate user input.

In another related system, the controller 20 is programmed to administer CNFS at a predetermined time following a start time manually inputted into the controller 20. It should also be noted that for system 400, or 100, 200, or 300, the controller may be equipped with a timer component 29. In this embodiment, the need for component 24' is alleviated, since the controller 20 and timer component 29 are sufficient to coordinate provision of CNFS at the appropriate time during a given scenario. This is discussed with respect to Example 2 (performance enhancement) in the Examples section below.

It should be noted that reference to a any component of systems 100, 200, 300 or 400 in singular form is not intended to be limiting, and may take the form or a plurality of the described components that work together to carry out the intended function. For example, user activity output monitoring component 24 may comprise a plurality of sensors, either of same type or of different types. For example, the given system may include a sensor 24' such as an accelerometer, GPS or other location detector that is positioned on the user 12, and may also user activity output monitoring component 24 such as a camera or microphone to detect user movement or sounds.

Figure 5:
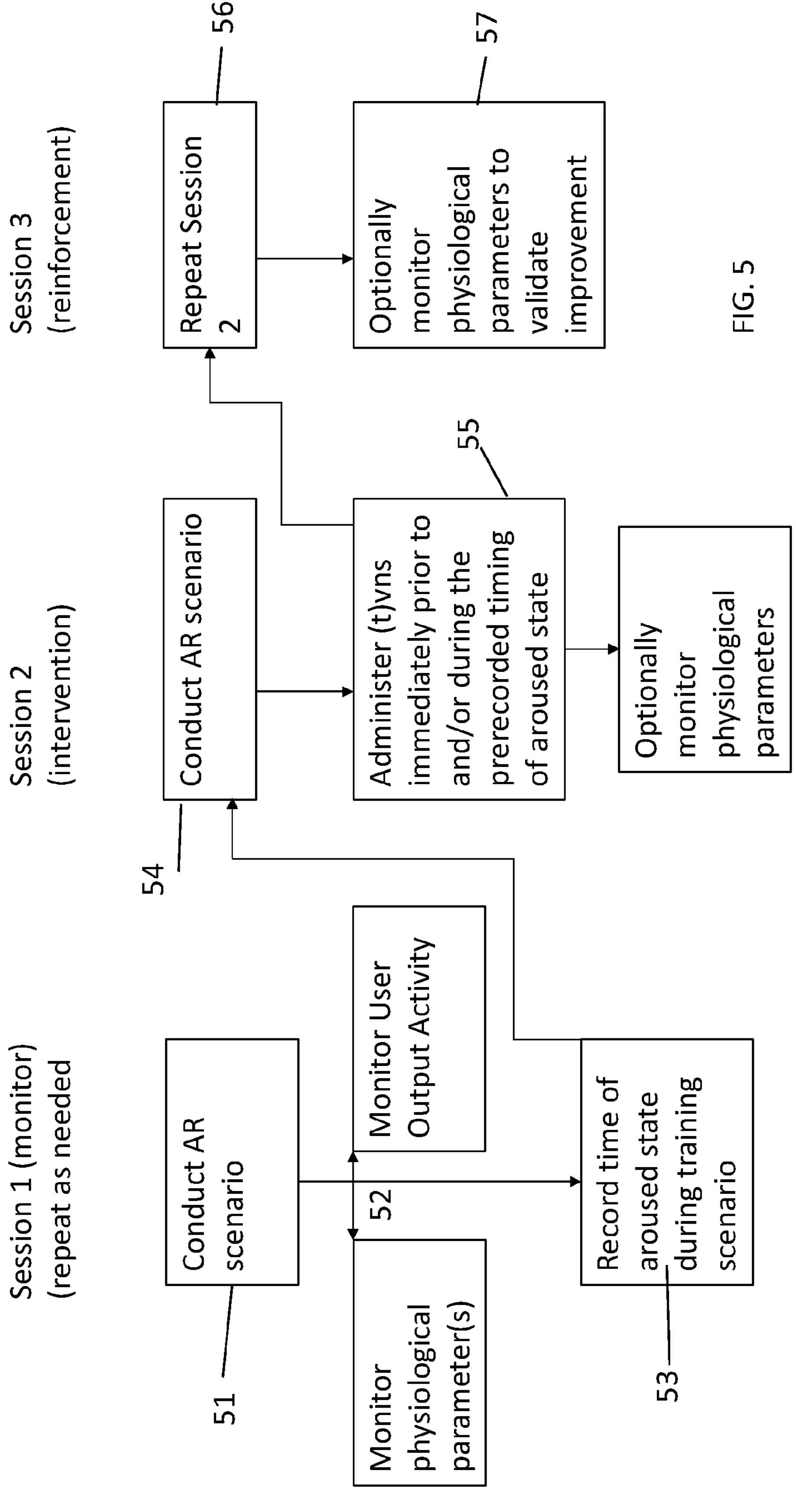
FIG. 5 provides a flow diagram of a training method that implements (t)VNS.

Turning to FIG. 5, a flow diagram is presented representing exemplary steps in a method of administering CNFS to a user using the system 100, 200 or 300 described above. The method involves a series of sessions. In session 1, step 1 51 involves presenting an AR scenario to the user 12. Step 2 52 involves monitoring physiological parameter(s) and/or user activity output during the AR scenario. In step 53, the controller records the time at which the user exhibits an aroused state. Subsequent to session 1, session 2 is initiated that involves step 1 54 where the AR scenario of session 1 is initiated. Step 2 55 involves administering (t)VNS at a time prior to the prerecorded timing of the aroused state, and/or at or during the prerecorded timing of the aroused state. During session 2, physiological parameters are optionally monitored. Subsequent to session 2, session 3 is initiated that involves step 1 56 of conducting the AR scenario of session 1 and 2, and step 2 57 of administering (t)VNS immediately prior to, and/or during the prerecorded time of the aroused state. Physiological parameters are optionally monitored to validate whether the (t)VNS improves (reduces) the aroused state during the AR scenario. Session 3 can be repeated as needed to further reinforce and train the user. It will be understood based on the teachings herein that in situations where physiological parameters are monitored this information can be used to further tune subsequent stimulation. For example, physiological parameters monitored in session 2 can be used to adjust stimulation in session 3, and physiological parameters monitored in session 3 can be used to adjust stimulation in a repeated session.

FIGS. 6-8 illustrate a number of sleep training modes programmed into controller 20 of any of systems 100, 200, 300 or 400 described above. In a particular example shown in FIG. 6 using system 400, the controller 20 is programmed with a Sleep training mode 1 61 that involves step 1 62 of initiating a sleep scenario on controller 20 of system 400. The controller 20 includes a timer component 29 and step 2 64 involves monitoring time following initiation of step 1 62. At a predetermined time following step 1 62, step 3 66 involves administering (t)VNS. Typically, step 3 66 is conducted at about 10-360 min following initiation of step 1. The length of step 3 can be modified based on intended outcomes. In the context of training sleep latency, step 3 may involve stimulating for variable durations, in which case shorter durations would be more applicable or training into transition to a specific sleep stage (e.g., slow wave sleep) where longer durations are more applicable.

FIG. 7 shows another example where the controller 20 of system 100 or 200 is programmed with sleep mode 2 71. Sleep mode 2 71 involves step 1 72 of initiating a sleep scenario on a controller 20. Step 2 74 involves monitoring a physiological parameter of the user. Step 3 76 involves initiating (t)VNS upon detecting a physiological parameter at a predetermined level.

FIG. 8 shows another example where the controller 20 of system 200, 300 or 400 is programmed with sleep mode 3 81. Sleep mode 3 81 involves step 1 82 of initiating a sleep scenario on a controller 20. Step 2 84 involves monitoring supine status of the user. Step 3 86 involves initiating (t)VNS at a predetermined time following detection of the user in a supine position.

EXAMPLES

Provided below are examples pertaining to certain implementations of the technology.

Example 1: Bodyscan Meditation (BM)/Progressive Relaxation (PR) with (t)VNS

AR component provides an AR scenario relating to practice of meditation where the AR component provides meditative guidance (e.g. software/device/audio recording/video/computer, tv, or phone based tool). Optionally, BM/PR may be assisted under guidance of another practitioner.

A user is instructed to focus on or relax successive regions of their body (e.g. head→face→neck→shoulders, etc.). The instructions may be pre-recorded or preprogrammed, and may provide instructions in a predetermined sequence and time sections addressing different body regions Autonomic behavior (e.g. HRV, RSA, GSR) during this behavior is monitored and biofeedback may be provided to the user. Note, autonomic activity, particularly RSA, reflect the behavior of several brain networks. Stimulation with tVNS influences these brain networks, and changes in autonomic features may reflect brain network modification. Thus autonomic behavior hereafter refers to both peripheral and brain elements. Biofeedback may or may not be provided via a biofeedback component such as a visual display of a body (avatar) that indicates ANS behavior on the avatar (see unyte.com for an example of existing software programs that involve avatar representation meditative states). This demonstrates desirable vs. not autonomic nervous system (ANS) behavior, reflecting a desired neurophysiological state. During future sessions of BM/PR, (t)VNS is applied during the guided activity bm/pr at strategic times when focus on body regions resulted in less desirable ANS responses were generated in previous sessions. In conjunction with this, the user can also identify body regions that they believe are tight or unrelaxed (e.g. pelvic region, lower back, shoulders . . . ). The (t)VNS can involve both sensory subthreshold and suprathreshold stimulation. The (t)VNS provides a tool to assist the user to relax, with the goal of eventually achieving similar relaxed states without (t)VNS.

FIG. 9 is a diagram depicting implementation of a method for applying (t)VNS in relation to bodyscan meditation implementation. RSA is recorded 1000 over time 1001 as the subject is guided via a time coordinated guided meditation to focus on different parts of their body as indicated by 1002. As can be seen in 1000, the RSA drops below 5.5 $\ln(ms)^2$ while the subject is focusing on their chest 1003 and their pelvic region 1004. Also, as can be seen when the subject is guided to focus on their lower limbs the RSA curves upward back to 5.5 $\ln(ms)^2$. A deviation of RSA below 5.5 $\ln(ms)^2$ indicates anxiety. Based on the recording 1000, a stimulation program is customized to address the subject's anxiety.

In session 2, 1005 shows that (t)VNS stimulation will be administered at min 4 until min 6, and at min 8 until min 15, for example. In the graph shown in 1006, the bodyscan meditation is executed with the (t)VNS stimulation, which shows that the RSA profile is dramatically improved. The RSA is above 5.5 $\ln(ms)^2$ at min 4-5 and almost back above 5.5 $\ln(ms)^2$ at mins 9-11.

In Session 3, the stimulation program is adjusted based on the recorded RSA results of the Session 2, where stimulation has been narrowed down to 8-11 min as shown in 1007. As the bodyscan meditation is executed in Session 3, it can be seen in graph 1008 that the RSA levels at min 8-9 has been further improved and is above the first standard deviation below normative value (e.g. 5.5 $\ln(ms)^2$). Thus, this example shows how cranial nerve stimulation coordinated with bodyscan meditation can treat people who have suffered psychological and physical trauma affecting parts of their body, such as in sexual assault situations or combat injury situations.

Example 2: Performance Enhancement

The above generally described systems and methods may be provided with the goal of increasing performance of a user, and not necessarily for treating illness, pathology, disease, etc. This may be to reduce nervousness that is experienced in conjunction with certain activities such as sport activities, public speaking, or even in military training such as sniper/shooting training. It may be used for medical training to improve performance of conducting surgical procedures. Note, autonomic behavior is also affected by effort. When people have more difficulty learning or are exerting greater cognitive control (as in controlled versus autonomic processing—see attention literature) tVNS has a learning component and may assist in acquisition of new skills. Thus, detecting signs of effortful control as indicated by reduced RSA (e.g.), may enable a learning enhancement deployment at the appropriate time of need.

In a specific example relating to sports performance, one hypothetical involves a golfer that has developed erratic putting due to pressure and fear of failure. In this situation, any of systems 100, 200, 300 or 400 may be implemented. The golfer is instructed to conduct their pre-shot routine while the controller tracks t0 when the golfer starts their preshot routine and t1 when the golfer initiates the putt. In a subsequent session, the golfer then repeats the preshot routine and the controller administers (t)VNS at a time between t0 and t1. The duration of the (t)VNS can be modified to suit the routine of a given performer. The (t)VNS helps train the golfer to reduce their anxiety while they are about to initiate putts. Over the course of several sessions, the (t)VNS is reduced or ceased while the golfer is performing their preshot routine and initiating the shot. Ultimately, the golfer will be able to control their anxiety without the need for (t)VNS and utilize this during real life competition.

It will be understood that that the system implemented for performance enhancement can incorporate any further components or substitute components described herein as needed, such as the AR component, user activity output component, and/or physiological parameter monitoring components. For example, using the golfer situation, the AR component could display a golf green, spectators, and/or competitors, as well as noises from each that would be typically experienced during competition. A user activity output component in the form of a camera could be implemented to monitor spatiotemporal positioning of the golfer during the preshot routine and initiation the shot. The controller could initiate (t)VNS via an CNFS component at a strategic time based on the motion or positioning of the golfer during their preshot routine and shot initiation. For further accuracy, a physiological parameter monitoring component could be implemented to determine at what stage of the preshot routine the golfer begins to experience an aroused state. The controller could then strategically time provision of (t)VNS to reduce arousal before the golf shot is performed.

The above golfer example is one of numerous examples where the systems described herein can be implemented to increase performance of an activity. The operation of the system can be tailored to assist performance enhancement for a given activity such as public-speaking, shooting free-throws, military shooting, or for reducing phobias such a fear of heights, swimming, entering enclosed spaces, etc.

The systems and embodiments described herein can be applied to any *regimented* relaxation practice. Not just BM/PR. For example, any guided relaxation that is based on a pre-established timeframe (e.g. a recording). It has the advantage of not simply being responsive to ANS shifts, but prospectively. The prospective nature of this stimulation delivery means that 1. It can be deployed before the shift in ANS. 2. It can be deployed without requiring multiple seconds of data to be collected for RSA/HRV measurement to be derived that would then drive CNFS. The systems and embodiments herein may be applied to address certain triggers of an aroused state, including temporal-spatial triggers. For example, If a subject is aroused as they get near an airport gate (fear of flying), the system can be deployed based on geographic information or location. The same approach could be applied to a subject who is trying to quit alcohol as they approach an alcohol serving location.

It should be borne in mind that all patents, patent applications, patent publications, technical publications, scientific publications, and other references referenced herein are hereby incorporated by reference in this application in order to more fully describe the state of the art to which the present invention pertains.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the preceding definitions are provided.

While a number of embodiments of the present invention have been shown and described herein in the present context, such embodiments are provided by way of example only, and not of limitation. Numerous variations, changes and substitutions will occur to those of skill in the art without materially departing from the invention herein. For example, the present invention need not be limited to best mode disclosed herein, since other applications can equally benefit from the teachings of the present invention. Accordingly, it is intended that the invention be limited only by the spirit and scope of the appended claims. The teachings of all references cited herein are incorporated in their entirety to the extent not inconsistent with the teachings herein.

What is claimed is:

1. A system comprising a cranial nerve fiber stimulation (CNFS) component;

a physiological parameter monitoring component, wherein the physiological parameter monitoring component is configured to sense or measure physiological parameter signals from a user;

an augmented reality (AR) component, the AR component comprising headphones, a speaker, a monitor displaying video recordings, or a virtual-reality device, or a combination thereof; and a controller communicably connected to the CNFS component, the AR component and physiological parameter monitoring component, wherein the controller comprises a central processing unit, circuitry for receiving/sending electrical signals and/or user input, at least one memory device and wherein the controller comprises one or more software algorithms that control operation of the CNFS component and/or AR component;

wherein the controller is configured to direct the CNFS component to administer CNFS to the user at or before a predetermined time in an AR scenario provided to the user by the AR component, the predetermined time being a time at which an aroused state of the user was recorded during a prior iteration of the AR scenario provided to the user.

2. The system of claim 1, wherein the controller is configured to receive input from the AR component and transmit an output to the CNFS component.

3. The system of claim 1, wherein the controller is programmed to modify an intensity or duration of the CNFS to a level optimized to achieve the intended effect, while also reducing discomfort.

4. The system of claim 1, wherein the AR component provides sensory stimulation to the subject at targeted times during an AR scenario, wherein sensory stimulation comprises music, white noise, individually selected emotionally uplifting music to treat depression or enhance cognition; trauma-related virtual-reality stimulation, haptic stimulation of specific dermatomes for treatment of chronic pain syndromes; physical exercises; guided virtual-reality experiences or recorded video stimulation of athletic performances to enhance motor skills; guided mental exercise instructions to enhance cognitive skills; video-conferenced psychotherapeutic treatment (including cognitive behavioral therapy); guided imagery; guided meditation to enhance psychological skills; or guided simulations of social situations to enhance social skills or autism spectrum disorders.

5. The system of claim 1, further comprising a user activity output monitoring component communicably connected to the controller or AR component, or both.

6. The system of claim 5, wherein the user activity output monitoring component comprises a device that monitors user activity not pertaining to physiological parameters, and wherein user activity monitored by the user activity output monitoring component comprises movement, spatiotemporal positioning, sound, or facial expressions.

7. The system of claim 6, wherein the controller receives monitored user activity and controls, times or synchronizes AR and/or CNFS based on the received user activity.

8. The system of claim 5, further comprising a user wearable device communicably connected to the user activity output monitoring component or controller, or both.

9. The system of claim 8, wherein the wearable device comprises an accelerometer, tilt sensor, or color marker.

10. A method of using the system of claim 5 comprising conducting a first iteration of an AR scenario to a subject via the AR component;

detecting at least one physiological parameter of the subject from the physiological parameter monitoring component and/or a user activity of the subject from the user activity output monitoring component;

recording a time of an aroused state during the first iteration to produce a recorded arousal time;

conducting a second iteration of the AR scenario; and administering central nerve fiber stimulation prior to and/or during the recorded arousal time while conducting the second iteration.

11. The method of claim 10, further comprising monitoring for physiological parameter changes in response to administering central nerve fiber stimulation for the second iteration or third iteration.

12. The method of claim 10 further comprising conducting a third iteration of the AR scenario; and administering central nerve fiber stimulation prior to and/or during the recorded arousal time while conducting the third iteration.

13. A system comprising a cranial nerve fiber stimulation (CNFS) component;

an augmented reality (AR) component;

a controller communicably connected to the CNFS component and the AR component; and a user activity output monitoring component;

wherein the controller is configured to direct the CNFS component to administer CNFS to a user at or before a predetermined time in an AR scenario provided to the user by the AR component, the predetermined time being a time at which a user activity output of the subject was recorded during a prior iteration of the AR scenario provided to the user.

14. The system of claim 13, wherein the CNFS is strategically administered to reduce user anxiety, induce relaxation, and/or increase performance without the need for physiological monitoring.

15. The system of claim 13, wherein the user activity output comprises a certain movement or series of movements, positioning, expression or the like, without a need for physiological monitoring.

16. A system comprising a cranial nerve fiber stimulation (CNFS) component;

a user activity output monitoring component;

a physiological parameter component;

a timer component; and a controller communicably connected to the CNFS component and user activity output monitoring component, physiological parameter component, or timer component, or combination thereof; wherein (a) the system administers CNFS at or before a predetermined time of user activity output as detected by the user activity output monitoring component; or (b) the system administers CNFS at or before a predetermined time of an aroused state as previously determined by the physiological parameter component.

17. The system of claim 16, wherein the user activity output monitoring component comprises a sensor to detect sleep initiation, time of day, light, polysomnography signals, or electroencephalograph (EEG) signals, and wherein the user activity output comprises sleep initiation or assuming a supine position.

18. A method of using the system of claim 16 comprising conducting a first iteration of a bodyscan meditation by a subject;

recording at least one time at which during the bodyscan meditation a respiratory sinus arrythmia (RSA) of the subject drops below a predetermined threshold to generate at least one recorded anxiety event;

conducting a second iteration of the bodyscan meditation; and administering central nerve fiber stimulation at or before the recorded anxiety event time.

19. The method of claim 18, wherein the predetermined threshold comprises an RSA of 5.5 In $(ms)^2$, and/or wherein administering comprises administering central nerve fiber stimulation that is initiated within 1-2 minutes prior to the recorded anxiety event and is ceased within 1-2 minutes after the recorded anxiety event.

* * * * *